(12) United States Patent
Thomson et al.

(10) Patent No.: US 9,372,173 B2
(45) Date of Patent: Jun. 21, 2016

(54) ULTRASONIC TESTING PHASED ARRAY INSPECTION FIXTURE AND RELATED METHODS

(71) Applicant: Orbital ATK, Inc., Dulles, VA (US)

(72) Inventors: Clint D. Thomson, Smithfield, UT (US); Jeremy D. Palmer, Farmington, UT (US); Robert N. Andersen, Ogden, UT (US); Kenneth B. Riding, Perry, UT (US)

(73) Assignee: Orbital ATK, Inc., Plymouth, MN (US)

( * ) Notice: Subject to any disclaimer, the term of this patent is extended or adjusted under 35 U.S.C. 154(b) by 368 days.

(21) Appl. No.: 13/829,988

(22) Filed: Mar. 14, 2013

(65) Prior Publication Data

US 2014/0260630 A1    Sep. 18, 2014

(51) Int. Cl.
G01N 29/22    (2006.01)
G01N 29/24    (2006.01)
G01N 29/26    (2006.01)

(52) U.S. Cl.
CPC .......... *G01N 29/221* (2013.01); *G01N 29/2456* (2013.01); *G01N 29/2487* (2013.01); *G01N 29/262* (2013.01); *G01N 2291/0231* (2013.01); *G01N 2291/045* (2013.01); *G01N 2291/106* (2013.01)

(58) Field of Classification Search
CPC ................................................ G01N 2015/142
USPC .................................... 73/618, 641, 588, 628
See application file for complete search history.

(56) References Cited

U.S. PATENT DOCUMENTS 3,550,438 A    12/1970  Kapluszak
3,780,572 A *  12/1973  Rocha ................... G01H 3/125
                                                    310/317
3,795,801 A *  3/1974   Broussaud ............. G06G 7/195
                                                    324/76.33
3,802,533 A *  4/1974   Brenden .............. A61B 8/0825
                                                    181/176

(Continued)

FOREIGN PATENT DOCUMENTS

JP          04009149 A  *  1/1992
JP          H04 09149        1/1992

OTHER PUBLICATIONS

Inspection Technologies: Standard Phased Array Probes and Accessories, GE Measurement and Control [online] GEIT-20122EN Nov. 2012 [retrieved on Aug. 29, 2013] retrieved on the Internet at < http://www.ge-mcs.com/trans-selection-guide/brochures/GEIT_20122EN_Standaard_Catalogus.pdf> 28 pages.

(Continued)

*Primary Examiner* — John Fitzgerald
*Assistant Examiner* — Herbert K Roberts
(74) *Attorney, Agent, or Firm* — TraskBritt (57) ABSTRACT

An inspection fixture is provided that includes a fixture, a lens, an ultrasonic phase array, a mirror and a liquid supply connector. The fixture body includes an inner chamber and an opening to the inner chamber. The lens defines a portion of the inner chamber. The ultrasonic phase array generates ultrasonic signals and is positioned to send the ultrasonic signals through the lens. The mirror is received within the inner chamber and is positioned at 45° in relation to the lens to reflect the ultrasonic signals from the lens out an opening to an inspection area of a body to be inspected and to reflect returned ultrasonic signals from the inspection area to the lens. The liquid supply connector is in fluid communication with the inner chamber.

21 Claims, 12 Drawing Sheets

(56) References Cited

U.S. PATENT DOCUMENTS

| | | | | |
|---|---|---|---|---|
| 3,895,685 A * | 7/1975 | Gillette | B41J 2/285 | 181/0.5 |
| 3,924,453 A * | 12/1975 | Clark | G01N 29/043 | 73/622 |
| 4,200,858 A * | 4/1980 | Takashima | G01N 29/262 | 367/135 |
| 4,352,294 A * | 10/1982 | Perodjon | G01N 29/221 | 359/709 |
| 4,508,122 A * | 4/1985 | Gardineer | G10K 11/357 | 600/446 |
| 4,788,866 A * | 12/1988 | Tanimoto | G01H 9/00 | 73/606 |
| 4,848,159 A * | 7/1989 | Kennedy | G01N 29/265 | 73/588 |
| 5,282,472 A * | 2/1994 | Companion | A61B 1/042 | 600/463 |
| 5,419,196 A * | 5/1995 | Havira | G01N 29/221 | 73/623 |
| 5,421,200 A * | 6/1995 | Casarcia | G01N 29/223 | 73/628 |
| 5,596,989 A * | 1/1997 | Morita | A61B 8/12 | 600/437 |
| 5,698,787 A * | 12/1997 | Parzuchowski | G01N 29/2418 | 73/583 |
| 6,069,698 A * | 5/2000 | Ozawa | A61B 5/0062 | 356/511 |
| 6,588,278 B1 * | 7/2003 | Takishita | G01N 29/0645 | 73/609 |
| 7,496,456 B2 * | 2/2009 | Hiyama | G01N 29/06 | 702/39 |
| 8,087,298 B1 * | 1/2012 | DiMambro | G01N 29/226 | 73/629 |
| 2002/0043561 A1 * | 4/2002 | Tsikos | B82Y 15/00 | 235/454 |
| 2002/0093881 A1 * | 7/2002 | Kane | G01H 9/00 | 367/149 |
| 2003/0222977 A1 * | 12/2003 | Yoshino | H04N 13/0495 | 348/51 |
| 2005/0081636 A1 * | 4/2005 | Barshinger | G01N 29/262 | 73/606 |
| 2005/0093713 A1 * | 5/2005 | Orme | G03B 35/14 | 340/815.4 |
| 2006/0027021 A1 * | 2/2006 | Choi | G01H 17/00 | 73/579 |
| 2006/0042391 A1 * | 3/2006 | Georgeson | G01N 29/07 | 73/633 |
| 2006/0236768 A1 * | 10/2006 | Bentzel | G01N 29/043 | 73/596 |
| 2006/0272418 A1 * | 12/2006 | Maris | A61B 5/0097 | 73/606 |
| 2007/0157730 A1 * | 7/2007 | Ochiai | F22B 37/003 | 73/627 |
| 2007/0171508 A1 * | 7/2007 | Huibers | G02B 26/0841 | 359/291 |
| 2007/0227250 A1 * | 10/2007 | Kennedy | G01N 29/225 | 73/641 |
| 2008/0037695 A1 * | 2/2008 | Kono | G01N 29/0609 | 376/249 |
| 2008/0178678 A1 * | 7/2008 | Girndt | G01N 29/04 | 73/622 |
| 2009/0235749 A1 * | 9/2009 | Ehara | G01N 29/07 | 73/622 |
| 2010/0298688 A1 * | 11/2010 | Dogra | A61B 5/0084 | 600/407 |
| 2011/0268384 A1 * | 11/2011 | Akkaya | G01H 9/004 | 385/12 |
| 2011/0314920 A1 * | 12/2011 | Nongaillard | G01N 29/022 | 73/649 |
| 2012/0157837 A1 * | 6/2012 | Nagata | G01N 29/067 | 600/437 |
| 2013/0218490 A1 * | 8/2013 | Poirier | G01N 29/069 | 702/56 |
| 2013/0304251 A1 * | 11/2013 | Garvey | G01N 29/225 | 700/213 |
| 2014/0260630 A1 * | 9/2014 | Thomson | G01N 29/221 | 73/628 |

OTHER PUBLICATIONS

European Search Report for EP 14159097, dated Aug. 13, 2014, 5 pages.

* cited by examiner

ULTRASONIC TESTING PHASED ARRAY INSPECTION FIXTURE AND RELATED METHODS

BACKGROUND

Pi-bonded composite structures are used increasingly in military and commercial aircraft. Although pi-bonded composite laminates exhibit enhanced strength in comparison to conventional fastening methods, they are difficult to inspect for critical flaws. Furthermore, these structures tend to be large and geometrically complex, making conventional immersion ultrasonic and ultrasonic phased array inspections difficult or impossible. Finally, existing phased array hand-held fixtures do not allow complete inspection coverage of pi-bonds near joints, corners, and stiffeners.

For the reasons stated above and for other reasons stated below that will become apparent to those skilled in the art upon reading and understanding the present specification, there is a need in the art for an effective and efficient device and method for inspecting pi-bonded composite structures.

BRIEF SUMMARY

The above-mentioned problems of current systems are addressed by embodiments of the present invention and will be understood by reading and studying the following specification. The following summary is made by way of example and not by way of limitation. It is merely provided to aid the reader in understanding some of the aspects of the invention.

In one embodiment, an inspection fixture is provided. The inspection fixture includes a body, an ultrasonic phase array, a mirror, and a fluid supply connector. The body of the inspection fixture includes an inner chamber. The body further has an opening to the inner chamber. The ultrasonic phase array generates ultrasonic signals. The mirror is received within the inner chamber. The mirror is positioned to reflect the ultrasonic signals out an opening in the body to an inspection area of a body to be inspected and to reflect returned ultrasonic signals from the inspection area back to the ultrasonic phase array. The fluid supply connector is in fluid communication with the inner chamber.

In another embodiment, an inspection fixture is provided that includes a fixture body, a lens, an ultrasonic phase array, a mirror, and a liquid supply connector. The fixture body includes an inner chamber. The body further has an opening to the inner chamber. The lens defines a portion of the inner chamber. The ultrasonic phase array generates ultrasonic signals and is positioned to send the ultrasonic signals through the lens. The mirror is received within the inner chamber. The mirror is positioned at 45° in relation to the lens to reflect the ultrasonic signals from the lens out an opening in the body to an inspection area of a body to be inspected and to reflect returned ultrasonic signals from the inspection area to the lens. The mirror is tapered. The liquid supply connector is in fluid communication with the inner chamber.

In another embodiment, a method of inspecting pi-bonds in a composite structure is provided. The method includes generating ultrasonic signals with a ultrasonic phase array; directing the ultrasonic signals to a mirror in a chamber of a body that is filled with a column of liquid; reflecting the ultrasonic signals off of the mirror and through an opening in the chamber to an area to be inspected; and directing reflected ultrasonic signals off an area being inspected back to the ultrasonic phase array.

BRIEF DESCRIPTION OF THE SEVERAL VIEWS OF THE DRAWINGS

The present invention can be more easily understood and further advantages and uses thereof will be more readily apparent, when considered in view of the detailed description and the following figures in which.

In accordance with common practice, the various described features are not drawn to scale but are drawn to emphasize specific features relevant to the present invention. Reference characters denote like elements throughout the figures and the specification.

DETAILED DESCRIPTION

In the following detailed description, reference is made to the accompanying drawings, which form a part hereof, and in which is shown by way of illustration specific embodiments in which the inventions may be practiced. The embodiments are described in sufficient detail to enable those skilled in the art to practice the invention, and it is to be understood that other embodiments may be utilized and that changes may be made without departing from the spirit and scope of the present invention. The following detailed description is, therefore, not to be taken in a limiting sense, and the scope of the present invention is defined only by the claims and equivalents thereof.

Embodiments of the present invention provide improved inspection capabilities for ultrasonic phased array inspection for pi-bonded composite structures, co-cured stiffened structures, as well as other 90 degree joint bonded concepts (such as shear ties). Embodiments also provide inspection capabilities for acute and obtuse angled joints. In embodiments, a portable hand-held phased array scanning fixture (inspection fixture) is used to inspect pi-bonds. The fixture provides improved scanning coverage on pi-bonds as well as improved resolution. This is done, in embodiments, by using an ultrasonic lens to focus a phased array beam across a width of a sensor, through a water column, onto a tapered mirror that reflects the beam into hard-to-reach joints, seams, corners, and tapers of the pi-bond. The fixture is compact and able to handle bonds exhibiting tight geometries, acute angles, obtuse angles, and hat stiffeners.

Figure 1:
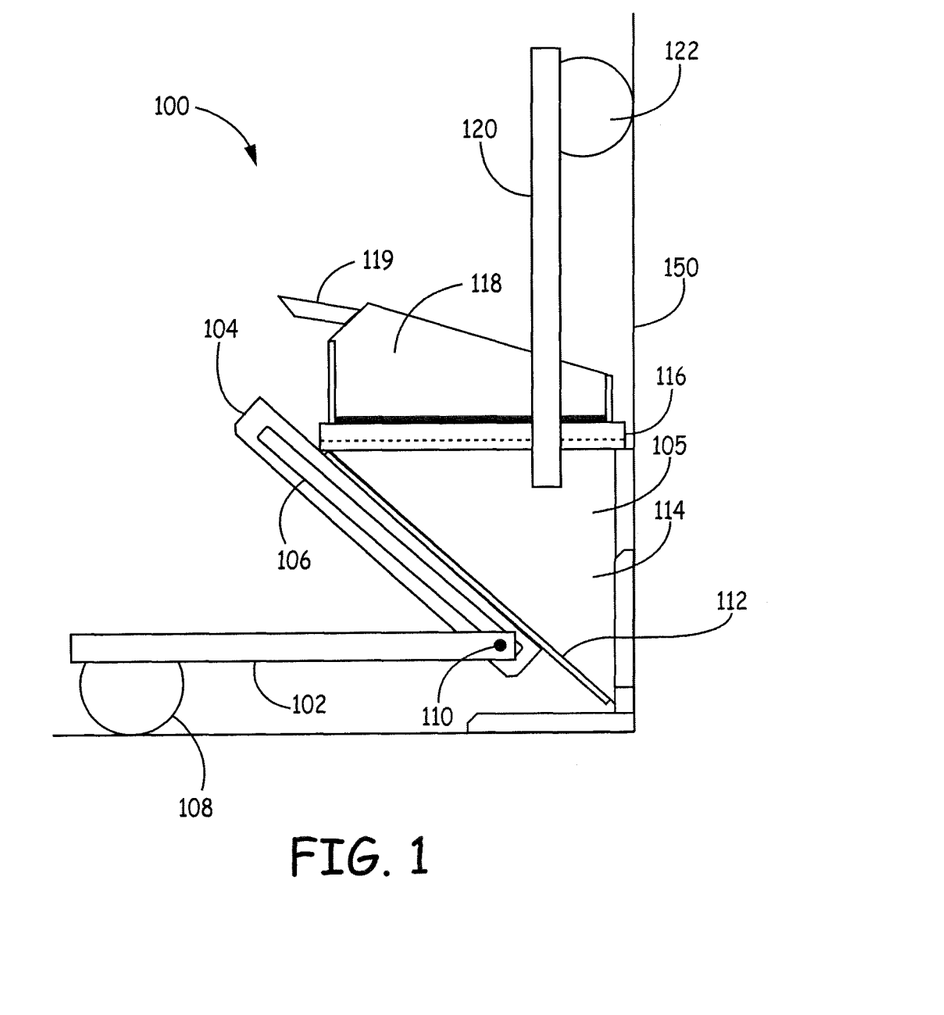
FIG. 1 is a side view illustration of an inspection fixture of one embodiment of the present invention.
Figure 2:
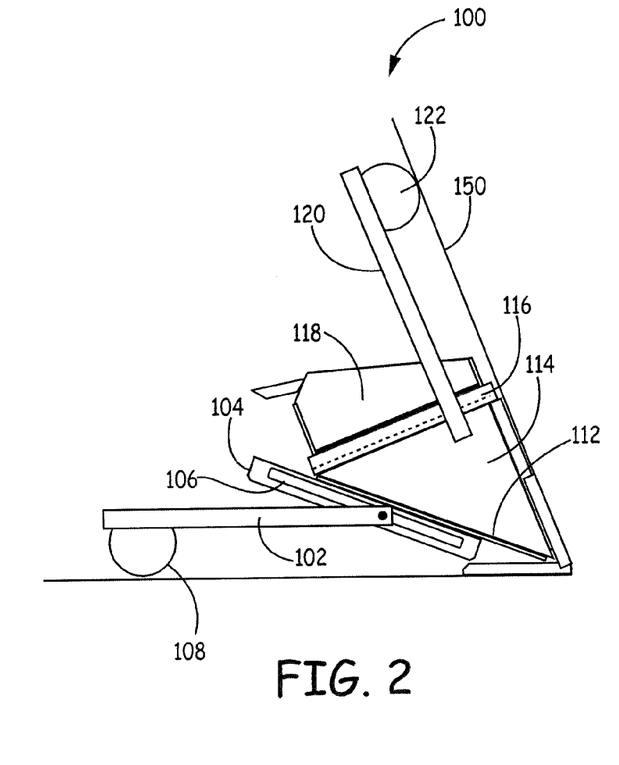
FIG. 2 is a side view of the inspection fixture of FIG. 1 in a different configuration.
Figure 3:
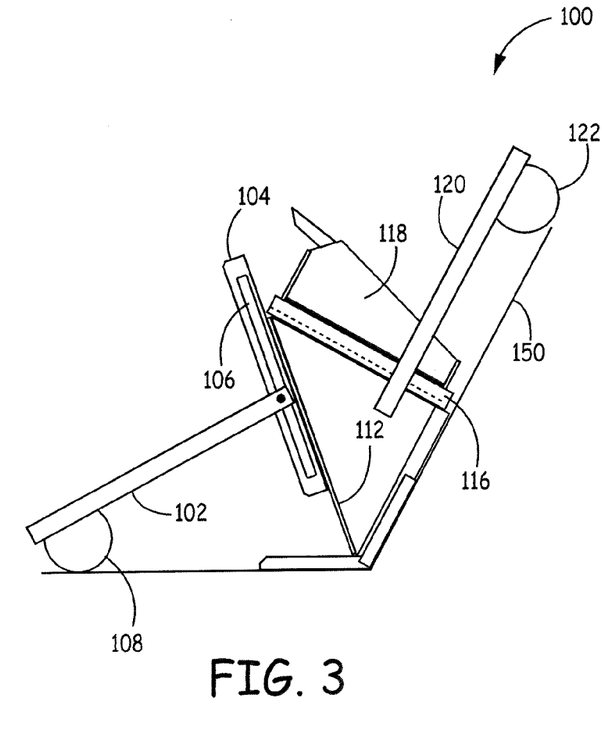
FIG. 3 is a side view of the inspection fixture of FIG. 1 in another configuration.

Referring to FIG. 1, a side view of the basic design of an inspection fixture 100 is illustrated. As illustrated, the inspection fixture 100 includes a first member 102. A roller bearing 108 is coupled proximate a first end of the first member 102. A second end of the first member 102 is slidably coupled in an adjustment slot 106 of a second member 104 via connecting rod 110. The inspection fixture 100 includes an inner chamber 105 that holds a column of water. In embodiments, (as discussed further below) a water (or fluid) supply is fed and maintained by an inlet water hose on a back of the fixture 100. A mirror 112 defines a portion of the inner chamber 105. The mirror 112, in this embodiment, is coupled to a side of the second member 104. The mirror 112, in one embodiment, is made from aluminum and in an embodiment is tapered. A focusing lens 116 further defines another portion of the inner chamber 114. In one embodiment, the focusing lens is a REXOLITE® focusing lens. However, other lens types can be used that are made from a variety of materials. The lens 116 provides improved lateral flaw resolution across the width of the phased array. Mounted to the lens 116 is an ultrasonic phase array sensor 118 that generates ultrasonic signals and receives reflected signals. The focusing lens 116 is positioned at 45° in relation to the mirror 112 so that ultrasonic waves generated by the ultrasonic phase array sensor 118 are reflected off the mirror 112 to an area of a structure to be tested. As discussed above, in some embodiments, the mirror 112 is tapered to allow inspection up to the pi-bond joint and also into corners. The water column is used for acoustic transmission and coupling of the ultrasonic signals. The ultrasonic signals that interact with the area to be inspected are reflected back off the mirror 112 back to the ultrasonic phase array 118. The reflected back ultrasonic signals are delivered via connection member 119 to a phased array receiver and processor (not shown) for processing. Also illustrated in FIG. 1, a third member 120 that has a first end coupled proximate the sensor 118 and lens 116 and a second end that is coupled to a roller bearing 122. The roller bearings 108 and 122 allow the inspection fixture 100 to move across a structure or part 150 to be inspected in a uniform manner. Referring to FIGS. 2 and 3, the flexibility of the inspection fixture 100 in this embodiment is illustrated. Because of the adjustable connection between the first member 102 and the second member 104, the inspection fixture 100 can be adjusted to inspect areas of structure 150 having corners that are less than 90° and more than 90°. Hence, in this embodiment, the adjustability between members 102 and 104 (that make up part of the body of the fixture 100) allow for joints of structures with many different configurations to be inspected with a single inspection fixture.

Figure 4:
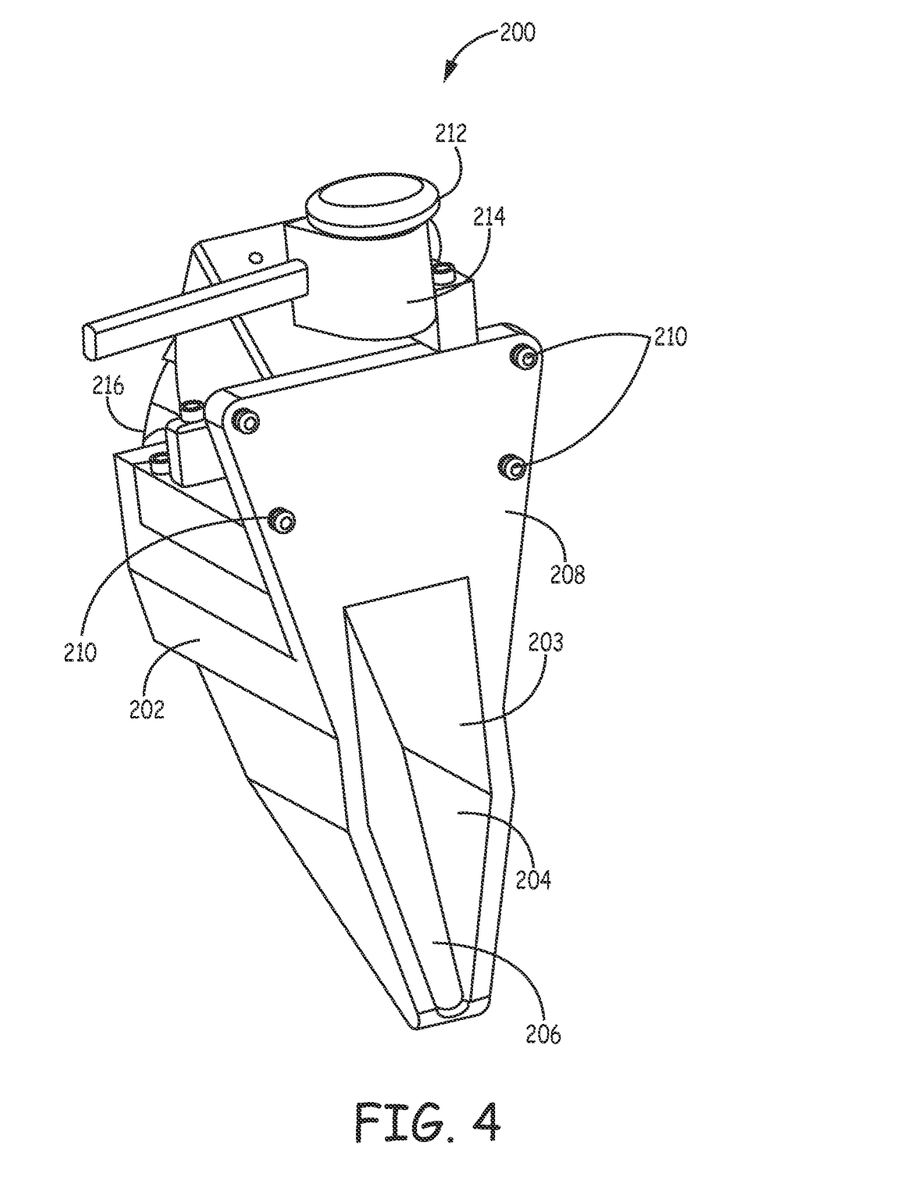
FIG. 4 is a front perspective view of another inspection fixture of an embodiment of the present invention.
Figure 5:
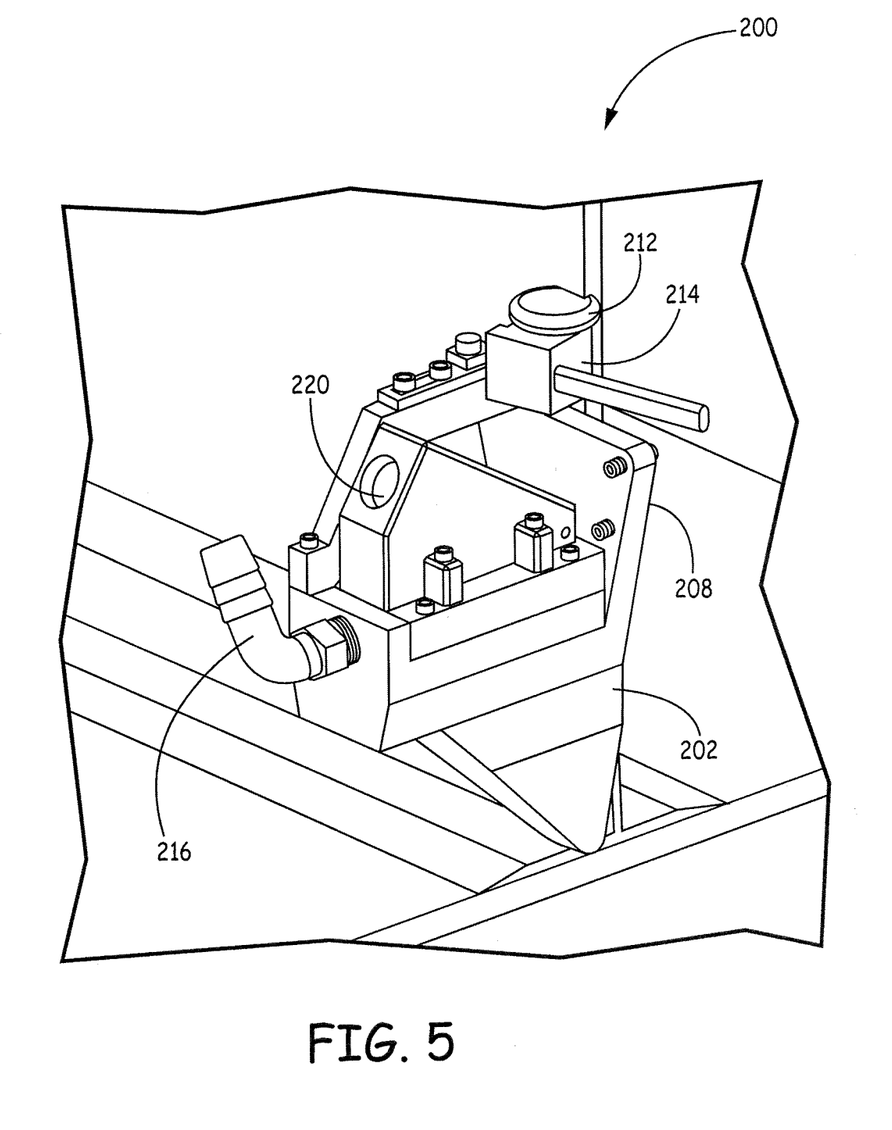
FIG. 5 is a first side view of the inspection fixture of FIG. 4.
Figure 6:
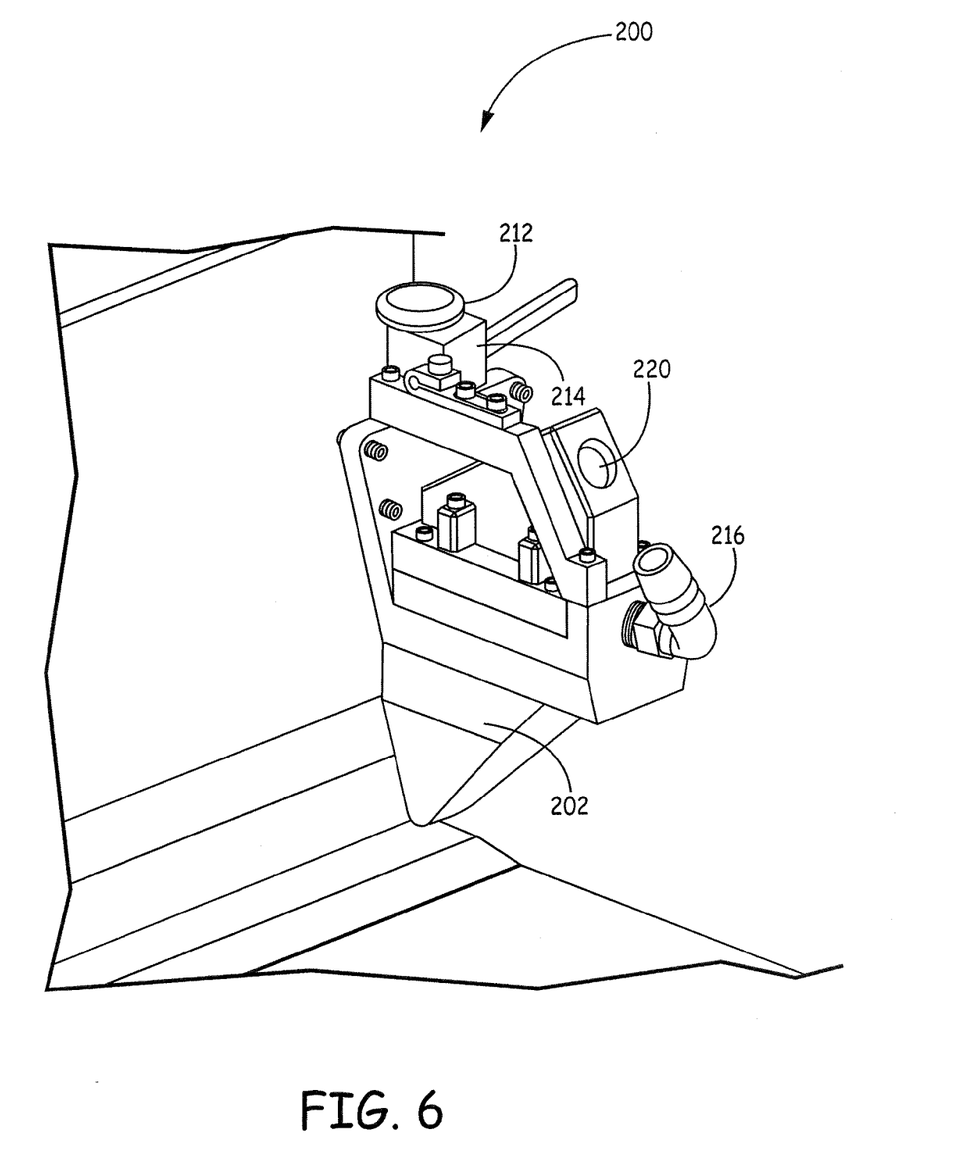
FIG. 6 is a second side view of the inspection fixture of FIG. 4.

Referring to FIG. 4, a front view of an inspection fixture 200 of another embodiment is illustrated. This embodiment includes a body 202 with an inner chamber 204. This view illustrates the opening 203 to the inner chamber 204. A mirror 206 is shown positioned within the inner chamber 204. A positioning plate 208 extends around the opening 203 to the inner chamber 204. In this embodiment, adjustable spacers 210 extend out from the positioning plate 208 a select distance to help position the inspection fixture 200 in relation to the structure being inspected. This embodiment further includes a roller 212 that is in communication with a linear encoder 214. The linear encoder 214 is mounted to the body 202 of the fixture 200. The roller 212 rides on laminates (i.e., structures to be inspected). The linear encoder 214 records positional information and is used to control timing of a phased array data acquisition signal. The linear encoder 214 is in communication with a processor (not shown in FIG. 4). Referring to FIGS. 5 and 6, respective side perspective views of inspection fixture 200 are illustrated as positioned to inspect a pi-bond of a T-shaped laminate structure. A water or fluid source, is coupled to a water connector 216 to provide a flow of water into the inner chamber 204 (FIG. 4), while the inspection fixture 200 is in use. Also illustrated is a supply/communication port 220 used at least in part to provide an ultrasonic energy to the fixture 200 and provide signals detected by the ultrasonic phased array to a processor system (not shown) via excitation/communication cable (such as cable 316 of FIG. 7).

Figure 7:
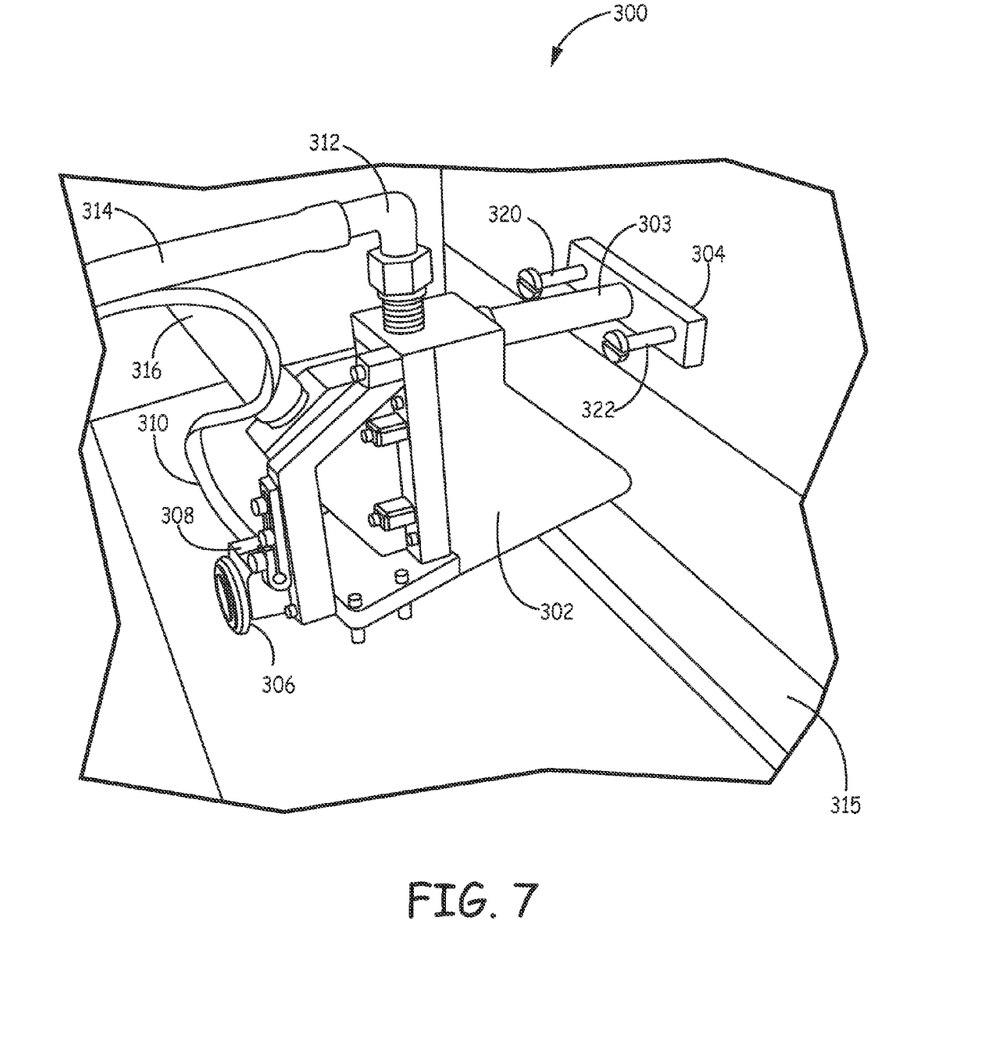
FIG. 7 is a side perspective view of an inspection fixture of another embodiment of the present invention.
Figure 8:
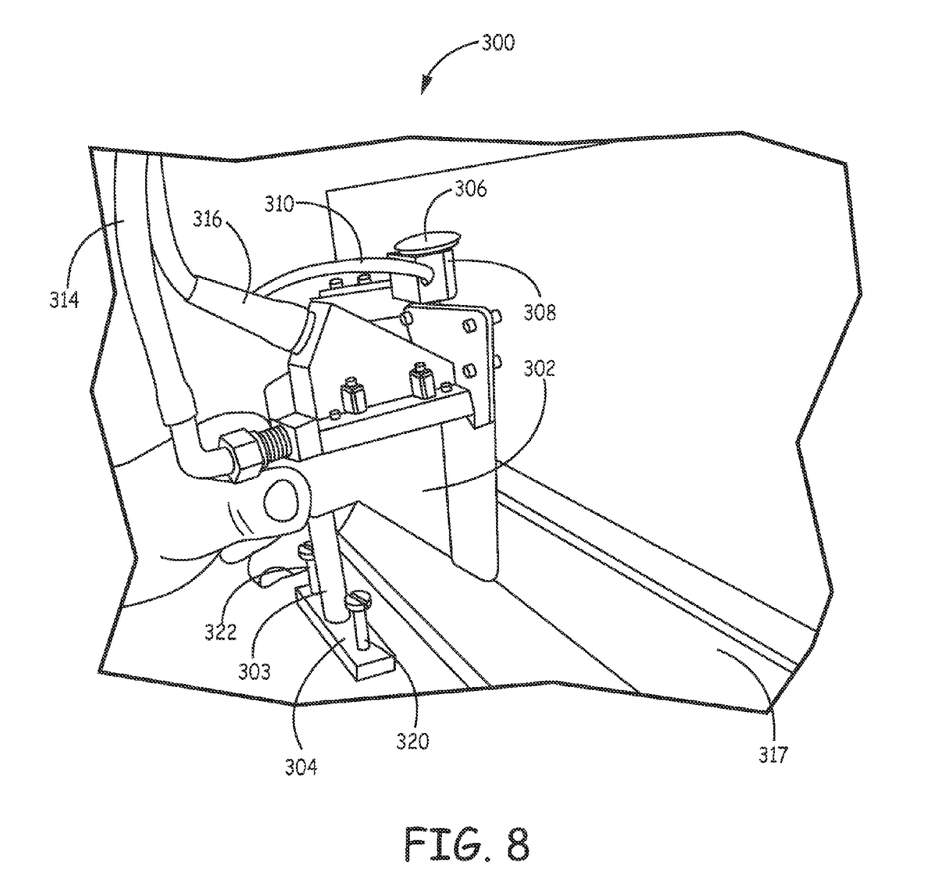
FIG. 8 is another side view of the inspection fixture of FIG. 7 shown in a different position.

FIG. 7 further illustrates another embodiment of an inspection fixture 300. FIG. 7 further illustrates that the fixture 300 can be positioned to inspect a bottom joint portion 315. Inspection fixture 300 includes a body 302. Attached to the body 302 is a spacer assembly that includes a spacer rod 303 that extends from the body 302. A spacer bar 304 is attached to the end of the spacer rod 303. Adjustable spacers 320 and 322 are threadably engaged to the spacer bar 304. The adjustable spacers 320 and 322 are used to adjust fixture standoff and angle with respect to the laminate and pi bond. An optional "riding" cart can be attached to the fixture 300 to facilitate scanning. FIG. 7 further illustrates a roller 306 and linear encoder 308 that is in communication with a processor (not shown in FIG. 7) via communication channel 310. Also illustrated is an ultrasound communication channel 316 that provides a path for the ultrasonic energy and a communication path to the processor. Further shown is a water supply 314 that is coupled to a water connector 312 to provide a water flow to an inner chamber. FIG. 8 illustrates the inspection fixture 300 in a different position to inspect a different portion 317 of the pi-bond.

Figure 9:
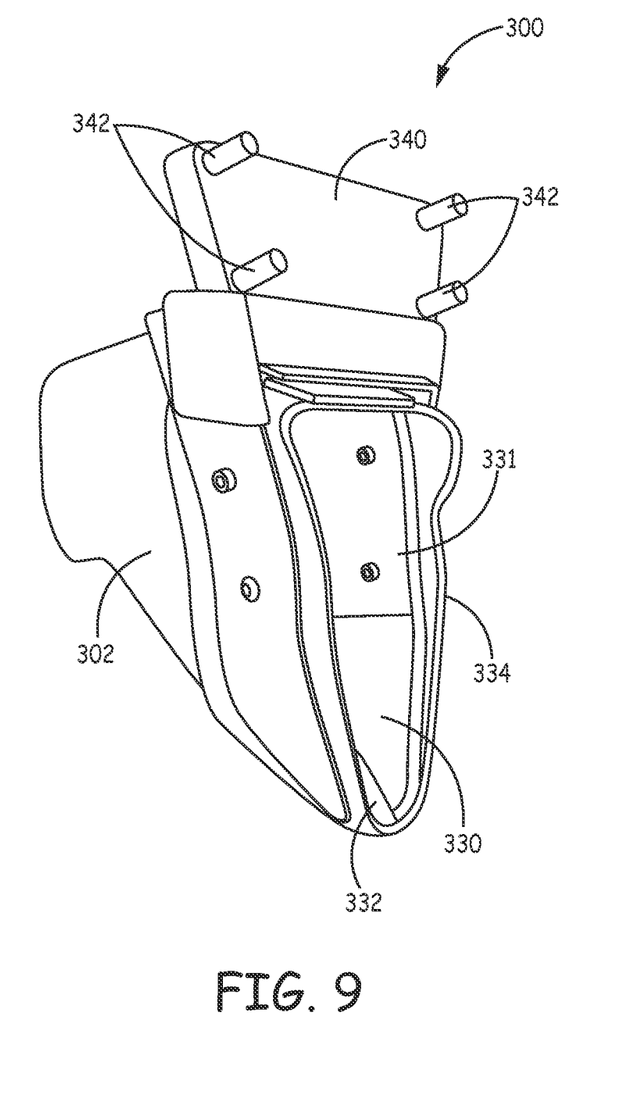
FIG. 9 is a front perspective view of the inspection fixture of FIG. 7.
Figure 10:
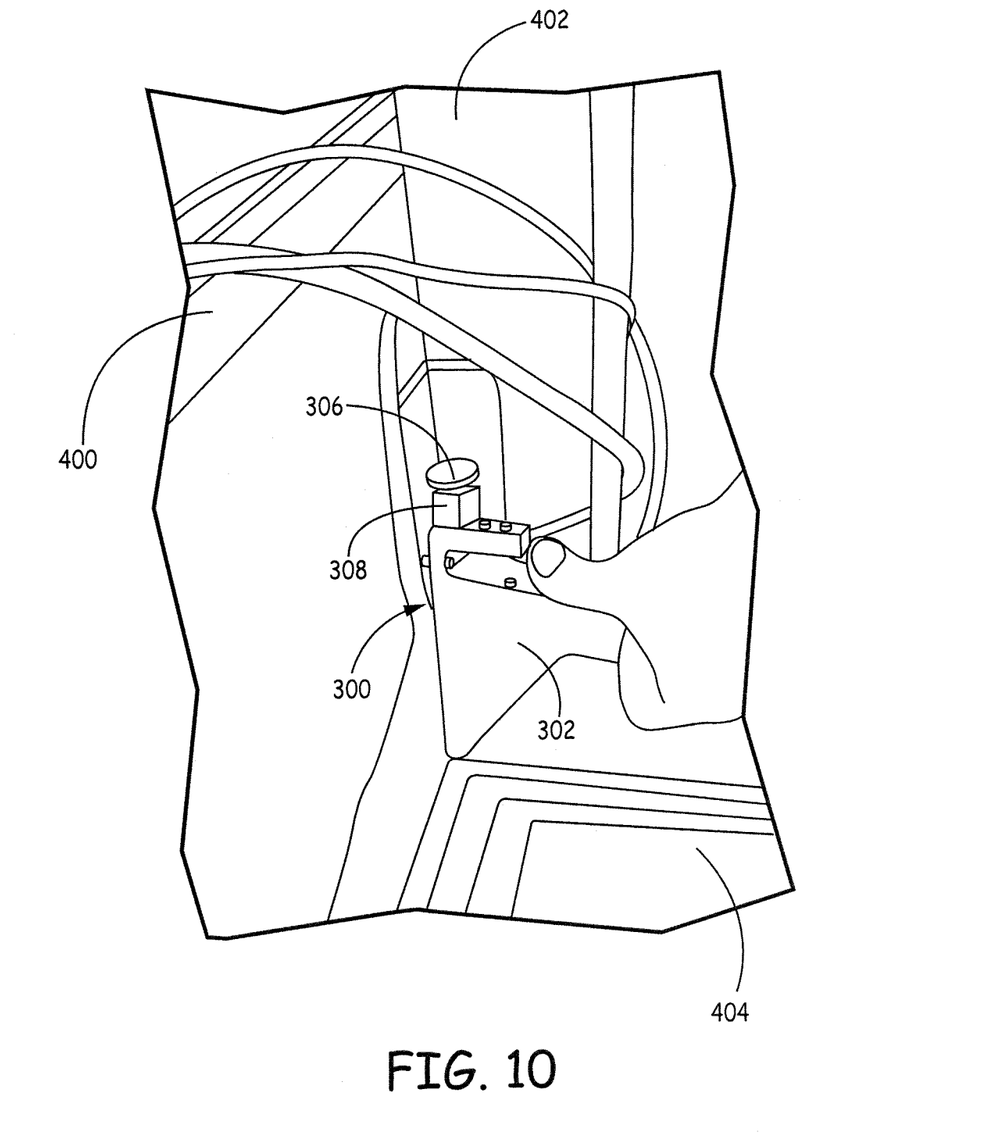
FIG. 10 is a side view of the inspection fixture of FIG. 7 in use in a corner.

FIG. 9 illustrates a front perspective view of the inspection fixture 300. This view illustrates the inner chamber 330 and the mirror 332 positioned within the inner chamber 330. In this embodiment, a skirt 334 is mounted around at least a portion of an opening 331 to the inner chamber 330. The skirt 334 is used to maintain water column pressure and stability, as well as to conform to uneven and rough pi-bond and laminate geometries. In one embodiment, the skirt is a porous membrane. Also illustrated in this view is spacing plate 340 that includes adjustable spacers 342 to position the fixture 300 at a desired location in relation to the structure to be inspected. FIG. 10 illustrates how the inspection fixture 300 can work to inspect a corner formed by structures 400, 402 and 404.

Figure 11:
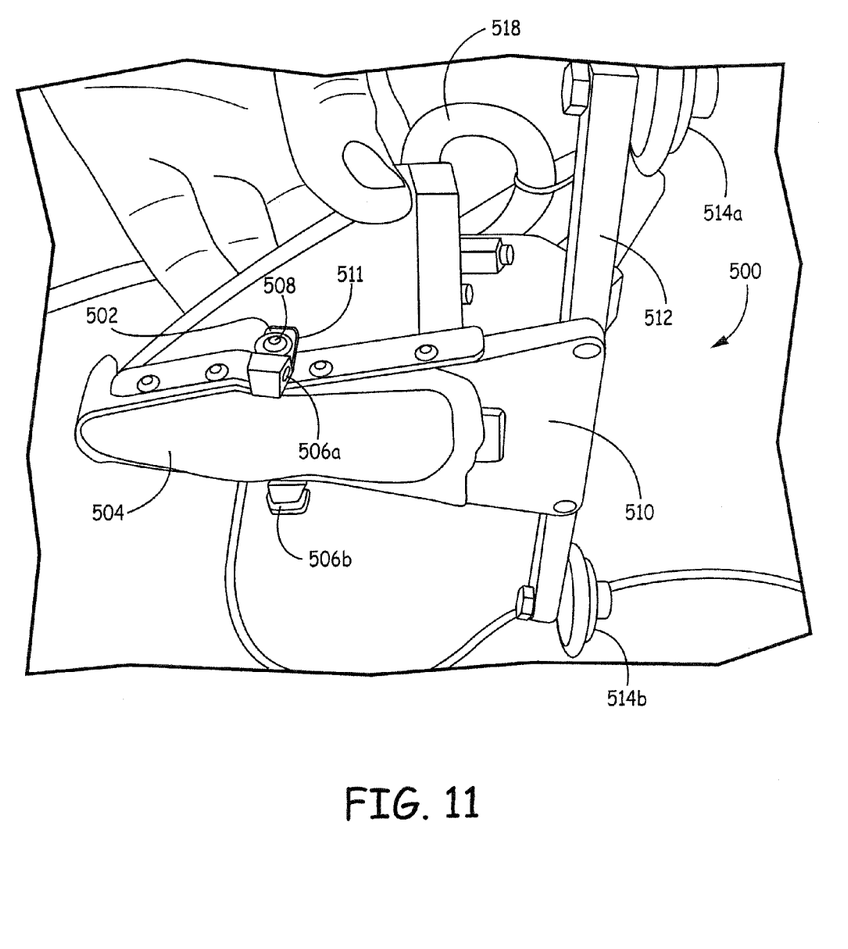
FIG. 11 is a front perspective view of an inspection fixture of another embodiment.
Figure 12:
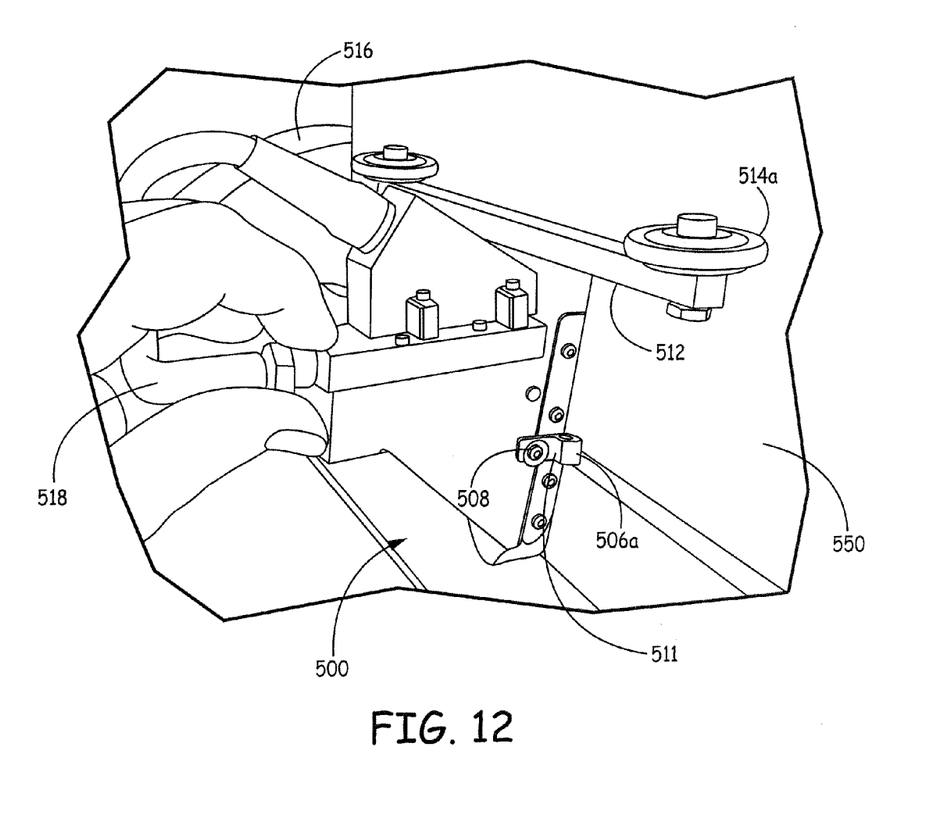
FIG. 12 is a side view of the inspection fixture of FIG. 11 in use.

Another embodiment of an inspection fixture 500 is illustrated in FIG. 11. In this embodiment, a porous membrane 504 covers up an opening to a chamber in a body 502. The porous membrane 504 is used to maintain the coupling of the acoustic transmission with the water column. This embodiment includes spacers 506a and 506b that are coupled to the body 502. As shown, spacer 506a is coupled to the body 502 via bracket 511 and fastener 508. The spacers 506a and 506b provide a spacing between the body 502 and a structure 550 being inspected, as illustrated in FIG. 12. The spacing protects the integrity of the porous membrane 504 during inspection and maintains the porous membrane 504 in a consistent configuration during inspection across the structure 550. The inspection fixture 500 of this embodiment also includes an arm 512 extending from a positioning plate 510. Attached to opposite ends of the arm 512 are bearings 514a and 514b, which in this embodiment, are used as spacers as well as wheels to assist in moving the inspection fixture 550 across the structure 550. FIG. 12 also shows an excitation/communication cable 516, which is coupled to an ultrasonic phase array of the inspection fixture 500. Also illustrated is a water supply conduit 518 of the inspection fixture 500.

Figure 13:
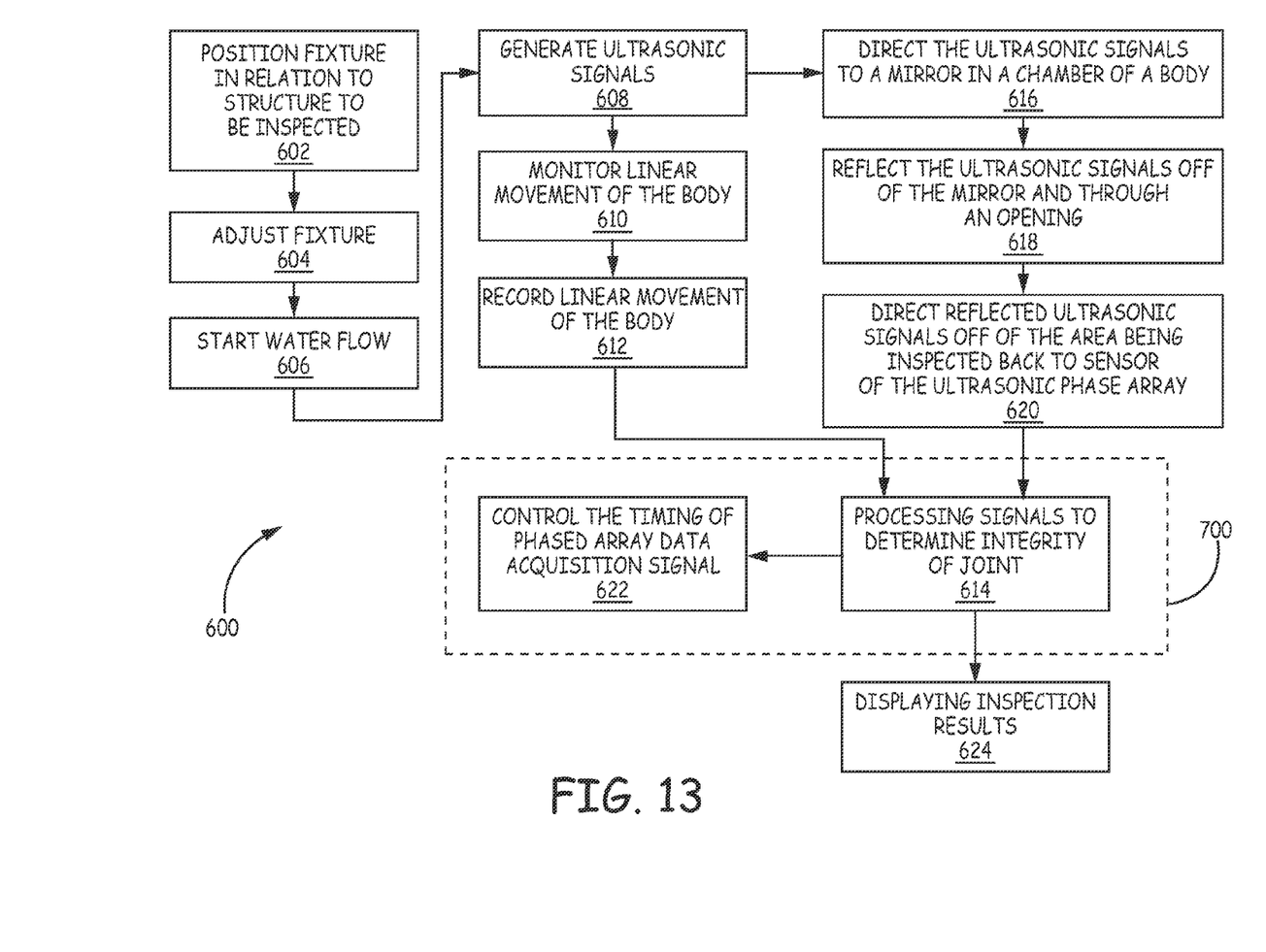
FIG. 13 is a flow diagram illustrating the steps of inspection of an embodiment using a fixture of the present invention.

Referring to FIG. 13, an inspection flow diagram 600 of one embodiment is illustrated. The process starts by positioning the fixture in relation to the structure to be inspected (602). The fixture standoff and angle, with respect to the bond being inspected, is then adjusted (604). A liquid flow is then started, which in one embodiment is a flow of water (606). Ultrasonic signals are then generated (608). Linear movement of a body of the inspection fixture is monitored (610) and recorded (612). This information is provided to processor 700 that uses the information to control the timing of phased array data acquisition signals (622). Further, the process directs the ultrasonic signals to a mirror in a chamber of the body (616). The ultrasonic signals are reflected off the mirror and through an opening in the chamber to a joint area to be inspected (618). Reflected ultrasonic signals off the area being inspected are directed back to a sensor of the ultrasonic phase array by the mirror (620) and the sensed information is passed on to the processor 700. The processor 700 processes the signals from the sensor to determine the integrity of the joint (614). Results of the determination are displayed to a user (624). The results can then be used to determine if the part passes inspection.

Although specific embodiments have been illustrated and described herein, it will be appreciated by those of ordinary skill in the art that any arrangement, which is calculated to achieve the same purpose, may be substituted for the specific embodiments shown. This application is intended to cover any adaptations or variations of the present invention. Therefore, it is manifestly intended that this invention be limited only by the claims and the equivalents thereof.

The invention claimed is:

1. An inspection fixture, comprising:
   a fixture body including an inner chamber and an opening to the inner chamber, an inspection side of the fixture body configured to juxtapose an inspection area of a body to be inspected, the inspection side of the fixture body exhibiting a substantially triangular shape comprising a first larger end having a first width and a second smaller end directly opposing the first larger end having a width less than the first width;
   an ultrasonic phased array configured to generate ultrasonic signals and positioned at the first larger end of the fixture body;
   a mirror received within the inner chamber, the mirror comprising a substantially planar reflecting surface exhibiting a taper extending along a length of the mirror from a first, relatively larger longitudinal end of the mirror positioned proximate the ultrasonic phased array and at the first larger end of the fixture body to a second, relatively smaller longitudinal end of the mirror positioned distal to the ultrasonic phased array and at the second smaller end of the fixture body, the first, relatively larger longitudinal end of the mirror opposing the second, relatively smaller longitudinal end of the mirror with two lateral tapering sides of the mirror extending and tapering inward from the first, relatively larger longitudinal end to the second, relatively smaller longitudinal end, the mirror positioned to reflect the ultrasonic signals out the opening to the inspection area of the body to be inspected and to reflect returned ultrasonic signals from the inspection area back to the ultrasonic phased array; and
   a fluid supply connector in fluid communication with the inner chamber;
   a first set of movement elements positioned proximate the first larger end of the fixture body configured to space the fixture body from the body to be inspected and to assist in movement of the fixture body fixture along the body to be inspected; and
   a second set of movement elements positioned proximate the second smaller end of the fixture body configured to space the fixture body from the body to be inspected and to assist in movement of the fixture body fixture along the body to be inspected.

2. The inspection fixture of claim 1, further comprising at least one adjustable member coupled to the body to adjust a position of the inspection fixture in relation to an item to be inspected.

3. The inspection fixture of claim 1, wherein the fixture body is configured to be adjustable to inspect joints of different degrees.

4. The inspection fixture of claim 1, further comprising a skirt coupled around at least a portion of the opening to the inner chamber.

5. The inspection fixture of claim 1, further comprising a porous membrane covering the opening to the inner chamber.

6. The inspection fixture of claim 1, further comprising a lens defining a portion of the inner chamber, wherein the ultrasonic phased array that generates ultrasonic signals is positioned to send the ultrasonic signals through the lens to the mirror.

7. The inspection fixture of claim 6, wherein the mirror is positioned at a 45° angle in relation to the lens.

8. The inspection fixture of claim 2, wherein the at least one adjustable member comprises at least one of a spacer, a roller, and a bearing.

9. The inspection fixture of claim 1, further comprising:
   a roller coupled to the fixture body; and
   a linear encoder in communication with the roller to record positional information.

10. The inspection fixture of claim 9, wherein the linear encoder is further configured to, at least in part, control timing of a phased array data acquisition signal.

11. An inspection fixture, comprising:
    a fixture body including an inner chamber, the fixture body further having an opening to the inner chamber;
    a lens defining a portion of the inner chamber;
    an ultrasonic phased array configured to generate ultrasonic signals and positioned to send the ultrasonic signals through the lens;
    a mirror received within the inner chamber, the mirror positioned at an acute angle in relation to the lens to reflect the ultrasonic signals from the lens out the opening to an inspection area of a body to be inspected and to reflect returned ultrasonic signals from the inspection area to the lens, an entirety of a reflective surface of the mirror comprising a taper extending along a length of the mirror from a first, relatively larger end of the mirror positioned proximate the ultrasonic phased array to a second, relatively smaller end of the mirror positioned distal to the ultrasonic phased array and opposing the first, relatively larger end with two lateral tapering sides of the mirror extending between the first, relatively larger end and the second, relatively smaller end, the taper enabling at least a portion of the fixture body and the mirror in the inner chamber of fixture body to be inserted into at least one of a pi-bond joint or a corner of an item to be inspected for inspection of the item; and
    a liquid supply connector in fluid communication with the inner chamber.

12. The inspection fixture of claim 11, further comprising at least one adjustable spacer coupled to the fixture body to adjust a position of the inspection fixture in relation to an item to be inspected.

13. The inspection fixture of claim 11, further comprising:
a roller coupled to the fixture body; and
a linear encoder in communication with the roller to record positional information.

14. The inspection fixture of claim 11, wherein the fixture body is configured to be adjustable to inspect joints of different degrees.

15. The inspection fixture of claim 11, further comprising a skirt coupled around at least a portion of the opening.

16. The inspection fixture of claim 11, further comprising a porous membrane covering the opening to the inner chamber.

17. A method of inspecting a composite structure, the method comprising:
generating ultrasonic signals with a ultrasonic phased array of an inspection fixture comprising a phased array beam across a width of the ultrasonic phase array, the inspection fixture comprising a first larger end housing the ultrasonic phased array having a first width and a second smaller end opposing the first larger end having a width less than the first width;
directing the ultrasonic signals directly from the ultrasonic phased array to a tapered mirror in a chamber of a body that is filled with a column of liquid, the tapered mirror having a first, relatively larger side positioned proximate the ultrasonic phased array and a second, relatively smaller side positioned distal to the ultrasonic phased array and positioned at the second smaller end of the inspection fixture;
positioning the second smaller end of the inspection fixture and the second, relatively smaller side of the mirror positioned at the second smaller end of the inspection fixture in a corner of an area to be inspected;
reflecting the ultrasonic signals off of the mirror and through an opening in the chamber to the area to be inspected; and
directing reflected ultrasonic signals off of the area to be inspected back to the ultrasonic phased array.

18. The method of claim 17, further comprising controlling timing of data acquisition signals from the ultrasonic phased array.

19. The method of claim 17, further comprising adjusting spacing members to position the body in a desired location during inspection.

20. The method of claim 17, further comprising monitoring linear movement of the body.

21. The method of claim 20, further comprising recording linear movement of the body.

* * * * *